(12) United States Patent
Bommannan et al.

(10) Patent No.: US 6,645,198 B1
(45) Date of Patent: Nov. 11, 2003

(54) SYSTEMS AND METHODS FOR REDUCING POST-SURGICAL COMPLICATIONS

(75) Inventors: D. Bommi Bommannan, Mountain View, CA (US); Michael D. Laufer, Menlo Park, CA (US)

(73) Assignee: Ntero Surgical, Inc., Palo Alto, CA (US)

( * ) Notice: Subject to any disclaimer, the term of this patent is extended or adjusted under 35 U.S.C. 154(b) by 225 days.

(21) Appl. No.: 09/665,730

(22) Filed: Sep. 20, 2000

Related U.S. Application Data

(63) Continuation-in-part of application No. 09/388,363, filed on Sep. 1, 1999, which is a continuation-in-part of application No. 09/271,268, filed on Mar. 17, 1999.

(51) Int. Cl.⁷ ................................................ A61B 18/18
(52) U.S. Cl. ............................. 606/34; 606/41; 606/42; 606/45; 607/101
(58) Field of Search ............................. 606/34, 41, 42, 606/45, 46, 47, 48, 49, 50; 607/101, 102

(56) References Cited

U.S. PATENT DOCUMENTS

| | | |
|---|---|---|
| 3,527,224 A | 9/1970 | Rabinowitz |
| 3,591,676 A | 7/1971 | Hawkins et al. |
| 3,667,472 A | 6/1972 | Halpern |
| 3,995,641 A | 12/1976 | Kronenthal et al. |
| 4,035,334 A | 7/1977 | Davydov et al. |
| 4,650,826 A | 3/1987 | Waniczek et al. |
| 5,213,580 A | 5/1993 | Slepian et al. |
| 5,328,687 A | 7/1994 | Leung et al. |
| 5,344,420 A | 9/1994 | Hilal et al. |
| 5,417,687 A | 5/1995 | Nardella et al. |
| 5,428,699 A | 6/1995 | Pon |
| 5,540,684 A | 7/1996 | Hassler, Jr. |
| 5,599,347 A | 2/1997 | Hart et al. |
| 5,690,675 A | 11/1997 | Sawyer et al. |
| 5,702,390 A | 12/1997 | Austin et al. |
| 5,711,958 A | 1/1998 | Cohn et al. |
| 5,728,143 A | 3/1998 | Gough et al. |
| 5,779,699 A | 7/1998 | Lipson |
| 5,782,900 A | 7/1998 | de la Rama et al. |

(List continued on next page.)

OTHER PUBLICATIONS

Bhatta, N., M.D., et al., "Injury and Adhesion Formation Following Ovarian Wedge Resection with Different Thermal Surgical Modalities," *Lasers in Surgery and Medicine* 13:344–352 (1998).

Mecke, H., et al., "Incidence of adhesions following thermal tissue damage," *Research in Experimental Medicine* ©Springer–Verlag (1991).

Mohsen, Amr A. . ., M.D., "Endocoagular Control of the Mesoappendix for Laparoscopic Appendectomy," *Journal of Laparoendoscopic Surgery*, vol. 4, No. 6 (1994).

Semm, K., "New Methods of Peliscopy (Gynecologic Laparoscopy) for Myomectomy, Ovariectomy, Tubectomy and Adnectomy," *Endoscopy 2*, George Thieme Publishers, (1979) 85–93.

*Primary Examiner*—Kevin Lee
(74) *Attorney, Agent, or Firm*—Pennie & Edmonds LLP

(57) ABSTRACT

The present invention provides systems and methods for applying RF energy to injured tissue, particularly the peritoneum, in order to prevent harmful post-surgical adhesions. One aspect of the invention is RF energy delivery systems employing trocars, which are designed for use in laparotomies and laparoscopies. Another aspect of the invention is an RF delivery system comprising a surgical sheet with one or more electrodes for delivering the RF energy to the injured tissue resulting from conventional surgical incisions into the abdominal wall. Additionally, another aspect of the invention provides methods for controlling the treatment dosage of RF heat to the injured tissue using parameters such as treatment time, change in tissue temperature, and change in tissue impedance.

17 Claims, 10 Drawing Sheets

U.S. PATENT DOCUMENTS

| | | |
|---|---|---|
| 5,791,352 A | 8/1998 | Reich et al. |
| 5,846,235 A | 12/1998 | Pasricha et al. |
| 5,906,609 A | 5/1999 | Wu |
| 5,914,345 A | 6/1999 | Slepian et al. |
| 5,944,718 A | 8/1999 | Austin et al. |
| 5,971,980 A | 10/1999 | Sherman |
| 5,992,418 A | 11/1999 | de la Rama et al. |
| 6,004,547 A | 12/1999 | Rowe et al. |
| 6,071,956 A | 6/2000 | Slepian et al. |
| 6,338,731 B1 | 1/2002 | Laufer et al. |

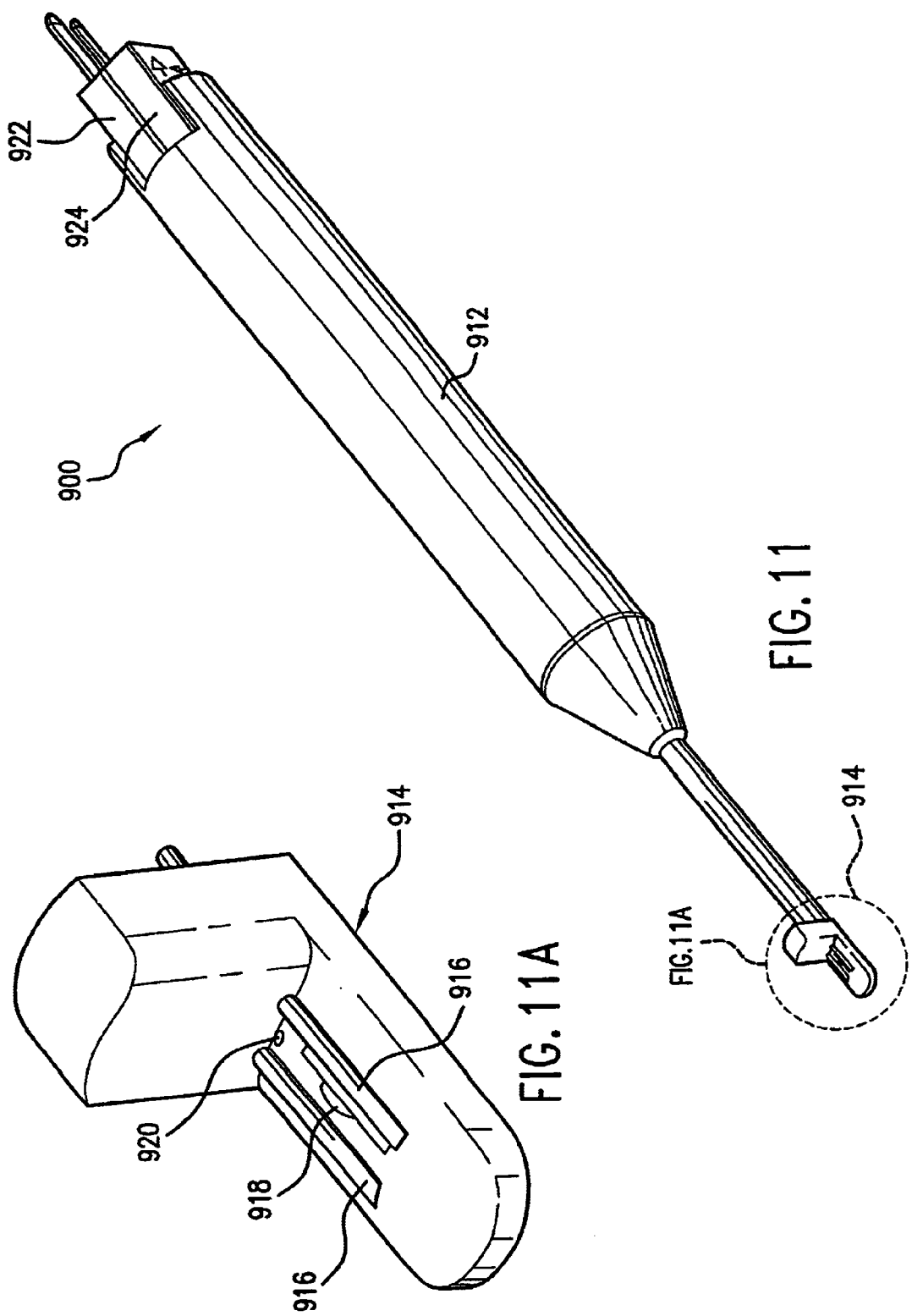

SYSTEMS AND METHODS FOR REDUCING POST-SURGICAL COMPLICATIONS

CROSS-REFERENCE TO RELATED APPLICATION

This application is a continuation-in-part of applicant's U.S. patent application Ser. No. 09/388,363, filed Sep. 1, 1999, which is a CIP of U.S. patent application Ser. No. 09/271,268, filed Mar. 17, 1999.

FIELD OF THE INVENTION

The present invention relates to methods and systems for reducing the incidence of complications that occur following many common surgical procedures. More particularly, the present invention relates to systems for reducing post-surgical complications that occur due to the natural tendency of the human body to form adhesions between injured areas within body cavities.

BACKGROUND

As a result of the healing process that follows abdominal, cardiothoracic, or arthroscopic surgery, complications frequently arise due to the natural tendency of the human body to form adhesions, which are connective tissue structures between injured areas within body cavities. Adhesions may form regardless of the nature of surgical procedures, whether done in a so-called minimally invasive fashion using laparoscopy or with a standard technique involving one or more relatively large incisions. These connective tissue bridges may cause various, often serious, complications. Usually the relief of post-surgical complications caused by adhesions requires another surgery. The subsequent surgery is complicated by the adhesions that were formed as a result of the previous surgery. The second surgery, itself, is likely to result in further adhesions and a continuing cycle of additional surgical complications.

One example of a problem that can be caused by adhesions is that following abdominal surgery, loops of intestine may become entangled or twisted about these adhesions. The entanglements may cause partial or total flow obstruction through the bowel, or may compromise the blood flow to and from the bowel. If such a condition is not relieved rapidly, the bowel dies and shortly thereafter the condition may cause death of the afflicted patient. As another example, adhesions that form in the pelvis after obstetric or gynecologic surgery may cause sterility as well as chronic pain.

Various suggestions have been made to avoid, reduce, or eliminate the formation of adhesions. For instance, standard surgical procedure in the United States often includes the steps of washing powder from surgical gloves prior to surgical operations, using powder-free gloves, and washing body cavities thoroughly prior to closing incisions. Another of the strategies that has been suggested to prevent adhesion formation is to loosely place a non-reactive barrier between an injured peritoneal surface and internal organs. Materials such as Interceed™ and Seprafilm™ and methods as described in U.S. Pat. No. 5,791,352 to Reich et al., have been advocated for minimizing adhesions. Also pourable (solidifying liquid gel material) substances have been suggested for preventing adhesion formation. These measures, unfortunately, have had only modest success in reducing the formation of post-surgical adhesions at the surgical locations. Therefore, it would be desirable to provide new and improved methods and apparatus that would eliminate or minimize adhesions.

SUMMARY OF THE PRESENT INVENTION

The present invention provides systems and methods for reducing the incidence of post-surgical tissue adhesions resulting from surgical incisions or perforations. In particular the present invention is adapted to treat surgical incisions or perforation to the peritoneum. The method of the present invention applies radio frequency (RF) energy to the edges of the peritoneal tissue that has been injured during surgery; the heat thus generated by RF energy minimizes or eliminates the formation of post-surgical adhesions.

During surgery, the peritoneum could be injured in at least two ways: (1) when punctures are made through peritoneum using a surgical device such as a trocar, and (2) with conventional incisions through the peritoneum. In accordance with the present invention, embodiments of delivery systems are provided which optimize the delivery of RF energy to incisions or punctures.

In one embodiment of the invention, the system for delivering the RF energy to the injured tissue is provided in conjunction with a trocar system. Electrodes for delivering RF energy to the injured tissue are positioned on the distal portion of the trocar sleeve. Further embodiments are provided deriving from this delivery system arrangement wherein the RF energy is provided by a separate RF source that is distant from the trocar or wherein the RF energy source is contained within a detachable unit that attaches to the top of a trocar. In the former embodiment, the source of electrical energy for generating RF signal can be an AC power source or a remotely located battery. In the latter embodiment, the detachable unit may contain both a small battery as well as the electrical circuitry to provide the RF energy to the electrodes. The batteries may be changed once exhausted, or if the batteries are integral to the detachable unit, the entire unit may be disposed of once the battery is exhausted.

In an alternative embodiment delivery electrodes may be placed on a separate member utilized in conjunction with a trocar or similar cannula. For example, electrodes may be positioned on a rod which is sized to be inserted through the cannula and extend distally to expose the electrodes for treatment. Alternatively, a sleeve may be provided with distal electrodes, wherein the sleeve is sized to be slipped over the outer diameter of the cannula and thus position the electrode for treatment.

In another embodiment of the invention, the system for delivering RF energy to incised peritoneum comprises electrodes embedded into an insulating surgical sheath. The underside of the sheath may have a weakly bonding adhesive layer that allows the sheath to attach to the skin. The adhesive allows the sheath to be placed and attached over the site of an incision before cutting occurs. Within the sheath, a configuration of electrodes is placed in position such that after the surgeon cuts through the sheath, the underlying skin and peritoneum, the electrodes are positioned over the site of incision. Within seconds or minutes of the incision, RF energy is delivered through the electrodes to treat the incised peritoneal tissue. Incision edges also may be treated by contact with electrodes on a hand held wand.

Methods are provided for the controlled delivery of optimal dosages of RF induced heat to the affected tissues. In accordance with an aspect of the invention, the change in the impedance of the heated peritoneal tissue can be used to determine the completion of treatment. Circuitry may be employed to measure the tissue impedance using the RF electrodes in order to determine when the tissue impedance has increased to a level where the treatment should be terminated. Another means for determining the end of treatment is by measuring the temperature of the surrounding tissue using a thermocouple. Once a predetermined temperature is reached, the sensing and control circuitry turns off the RF energy delivery to the electrodes. In another variation, the RF delivery is turned off after a predetermined time duration has been reached. A further refinement tracks both the temperature of the heated tissue and the duration of the RF energy delivery in order to determine the end of treatment.

BRIEF DESCRIPTION OF THE DRAWINGS

FIG. 11 is a perspective view of a hand held wand according to another embodiment of the invention.

DETAILED DESCRIPTION OF THE PREFERRED EMBODIMENT

The following description provides preferred system embodiments employing RF treatment of surgically injured tissue. There are two types of common surgical injuries to the tissue, in particular to the peritoneum and pleura: (1) punctures produced by trocars during laparoscopic surgery and (2) incisions made during laparotomies (open surgery). In accordance with the present invention, systems using RF for treating peritoneal injuries are provided. Additionally, methods for determining and controlling the extent of tissue heating are provided to optimize the RF treatment to the tissue.

Figure 1:
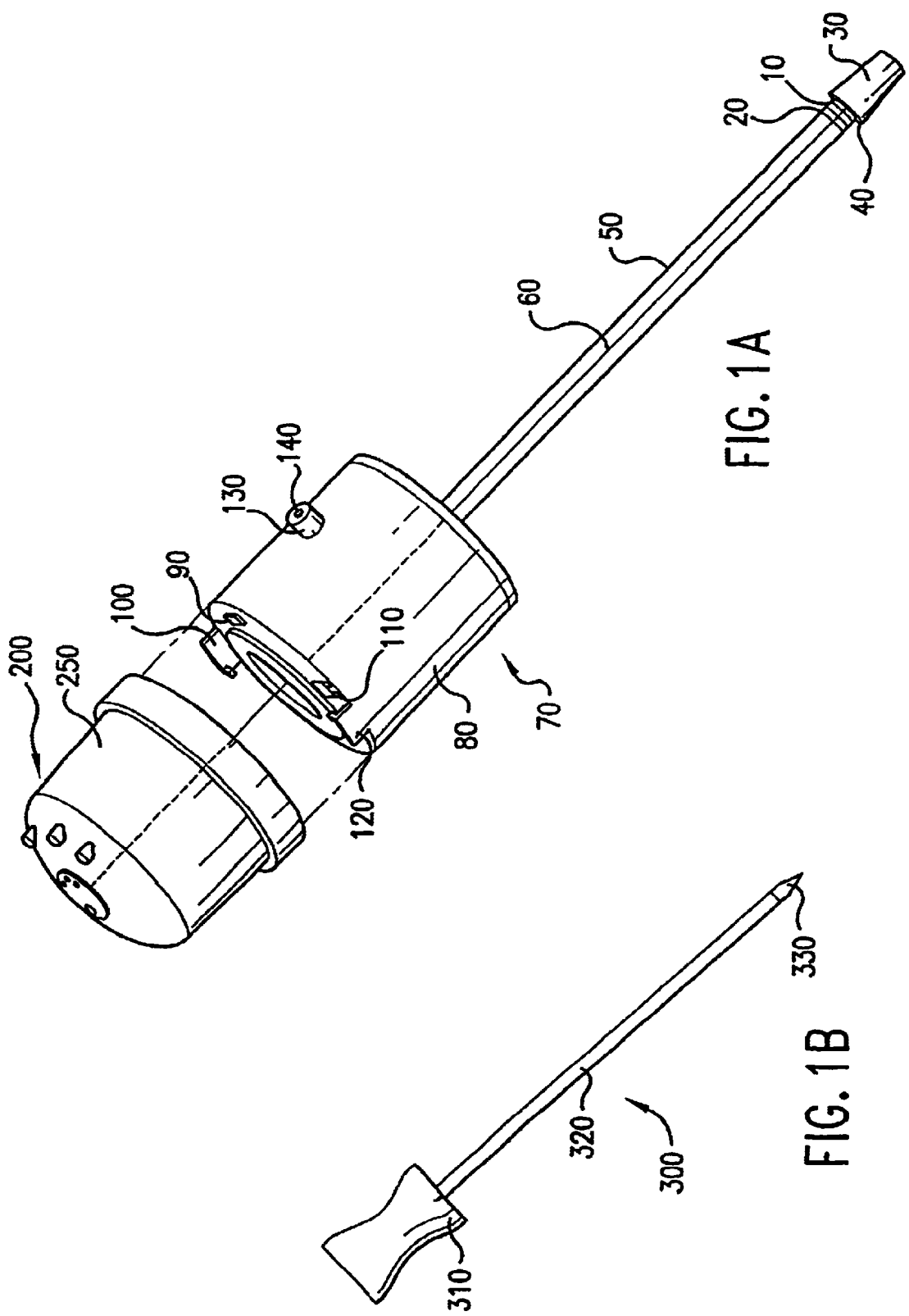
FIG. 1A shows a perspective view of the two-part trocar-based RF energy delivery system having a top detachable RF unit and a trocar sleeve which has a bipolar electrode arrangement, in accordance with the present invention.
FIG. 1B shows a perspective view of the obturator (puncturing tool) that is inserted into the trocar sleeve and functions as an assembly for puncturing the abdominal wall.

FIGS. 1A–B illustrates a trocar compatible RF energy delivery system using a bipolar electrode configuration. This system is used for laparoscopies, laparotomies and other minimally invasive surgery that require punctures through the peritoneum. In accordance with a preferred embodiment of the invention, this system comprises three separable components. One part is detachable RF unit 200. A second part is trocar sleeve 70 which connects to RF unit 200 using attachment means known in the art. And a third part is puncturing unit 300, called an obturator, which inserts into trocar sleeve 70. The means of attachment to lock detachable unit 200 with trocar sleeve 70 is provided by latches 100 and 120. Other means of attachment known to those skilled in the art may also be used. For example, a thread and screw pair, or clasps are but a few of the possible means of attachment. But generally, the means of attachment is preferably of a design which allows the surgeon to quickly lock and release the connections since reduction of surgical time is of the essence.

FIG. 1A shows trocar sleeve 70, which has a cylindrical top portion 80 and lower rod-like sleeve portion 50. The top portion has protruding latches 100 and 120. The rod-like sleeve portion is elongated to permit insertion into the body cavity, whereas the top portion has an enlarged diameter to permit manipulation of the trocar sleeve assembly. The trocar sleeve is hollow along its entire length including top portion 80 and rod-like portion 50. The rod-like portion ends at lip 40 formed by conical portion 30 at the distal end of the trocar. The presence of the lip helps position the sleeve relative to the peritoneum so that when the trocar is gently pulled out, the lip catches the edge of the peritoneum. First electrode 10 is close to the lip in order to be positioned near the injured peritoneum. Once conical portion 30 of the trocar has been inserted past the peritoneum, lip 40 prevents the sleeve from being pulled out of the abdominal wall during routine procedures such as inserting or removing laparoscopic instruments through the trocar.

As shown in FIG. 1A, electrodes 10 and 20 are mounted in a bipolar arrangement around the distal portion of the trocar sleeve near lip 40. The electrodes are preferably shaped as rings and are made of conductive materials such as stainless steel. The electrodes may be made of platinum, platinum-iridium, aluminum, carbon or other typical, body-compatible electrode materials. The two electrodes are shaped and mounted to fully encircle the sleeve and are spaced about a millimeter apart from each other. First electrode 10 is slightly smaller in width, and hence in surface area, than second electrode 20. The first electrode shown has a width preferably between about 0.5 to 3 millimeters and has a spacing of between about 0.5 to 5.0 millimeters. More preferably, the spacing between the electrodes should be between about 0.5 to 3.0 millimeters.

One or more thermocouples (not shown) can be optionally mounted to the distal end of the sleeve, preferably beneath second electrode 20, to measure the instantaneous tissue temperature at that site. The temperature measurements thus obtained may be used to control the delivery of heat to the target tissue.

Additionally, the rod-like portion 50 contains conducting wires connecting electrical contacts 110 and 90 with electrodes 10 and 20. Conducting wire 60 is shown on the outside of sleeve 50 and connects active electrode 10 with electrical contact 110. Wire 60 can also be placed within the wall of the sleeve or on the inside surface of the sleeve wall. Another conducting wire (not shown) connects the second, return electrode 20 with electrical contact 90. Another conducting wire (not shown) may be placed on the inside or outside surface of the sleeve wall or within the wall itself to connect a thermocouple that is located approximately at the location of electrode 10, but positioned directly beneath it.

Trocar sleeve top portion 80 has standard luer valve 130 with opening 140. The opening is used to inflate the cavity as known in the art in preparation for viewing with laparoscopy or for inserting therapeutic fluids such as antibiotics after the completion of a surgery.

As shown in FIG. 1A, the detachable unit 200 is made of a housing which encloses various circuitry. As shown in the system of FIG. 1A, the detachable unit is fully self-contained and includes a battery within the housing. Since a battery is used, the unit may be used more than a single lifetime of the battery by replacing the battery. Alternatively, the unit may be designed so it can be thrown away after the single battery is exhausted. The advantage of such design is that the unit can be made relatively inexpensively since it is only to be used once, and the unit does not need to be re-sterilized after its use. Alternatively, the unit may be constructed more robustly to last multiple battery cycles and to accept sterilization.

The detachable unit also contains an RF circuit to transmit energy through at least a pair of electrical contacts (not shown) on the underside of the housing 250 of detachable unit 200. The two contacts are preferably small rectangular pieces of conductive material which are complementary to electrical contacts 90 and 110, located on the trocar top portion 80. The two contacts on the underside of detachable unit 200 are positioned such that when the detachable unit 200 is locked with latches 100 and 120 to the trocar top portion 80, there is electrical communication between the two contacts in the detachable unit with complementary contacts 90 and 110. Moreover, once the detachable unit is locked to the trocar top portion, there is also electrical communication between the RF circuitry residing in detachable unit 200 and the electrodes 10 and 20.

Figure 2:
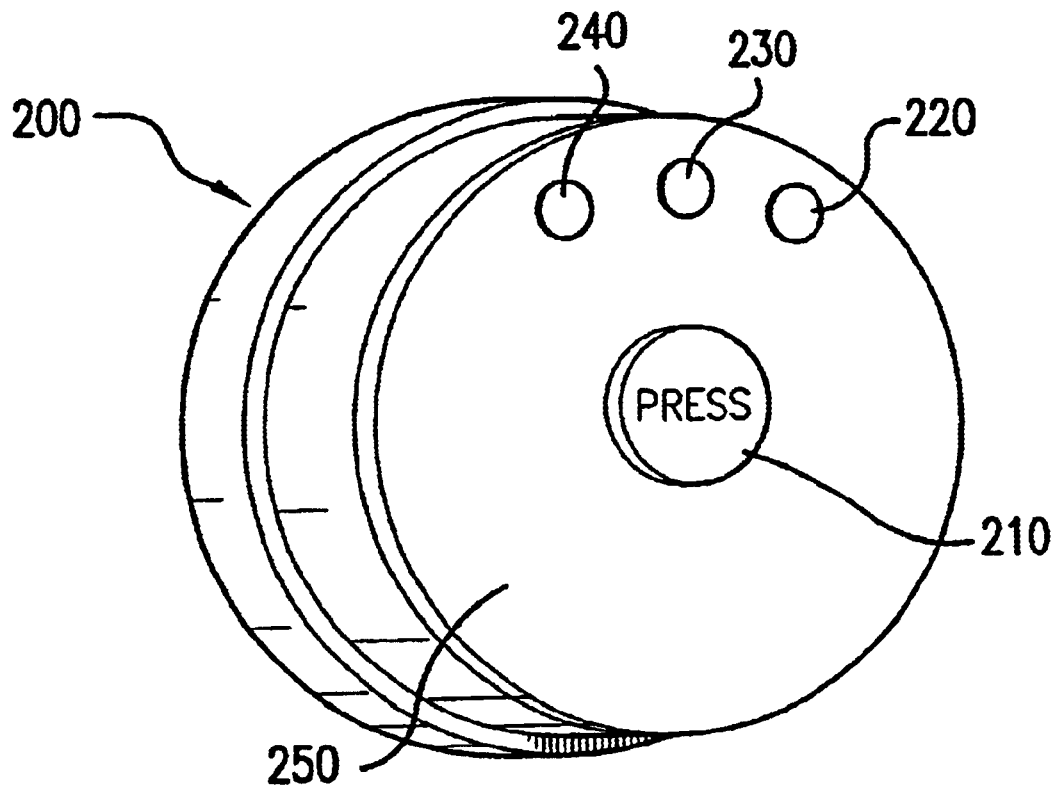
FIG. 2 shows a more detailed top perspective view of the detachable RF unit of FIG. 1A that fits over the trocar unit, in accordance with the present invention.

FIG. 2 shows a perspective top view of the housing 250 of the detachable unit 200 with greater detail. There is a push button 210 for turning the RF circuitry on in order to deliver RF energy to the electrodes located on the trocar sleeve. There are three indicator lights 220, 230 and 240, which indicate, respectively, that the treatment is finished, that the treatment is in progress, and that the circuitry is ready to initiate delivery of the RF energy. The top portion of the housing is made of materials known in the art such as plastic.

As shown in FIG. 1B, the third part of the system is an obturator 300 having a top cap 310 and a rod 320. The distal end of the rod 320 ends in a sharp tip 330. The rod 320 fits inside the trocar 70 and the tip 330 passes the conical portion 30 when inserted. Once mated, the cap portion 310 should be locked to trocar top portion 80 and the puncture unit tip 330 should be just exposed through the distal end of the conical portion 30. The materials to make the puncturing unit are standard. The cap 310 may be of sterilizable plastic and rod 320 a metal, such as stainless steel or aluminum, although alternatively, it may be made of other materials such as medical grade plastics.

The foregoing RF energy delivery system is used in operation according to the following steps. The target skin area in the abdominal wall is prepared using the usual procedures in preparation for surgery such as shaving the skin and applying a topical antibacterial solution. Under sterile conditions, rod 320 is inserted into trocar 70 such that tip 330 is exposed. The assembly then is used to puncture a hole through the prepared abdominal skin and through the peritoneum. The assembly is withdrawn slowly until trocar lip 40 abuts against the edge of the peritoneum. The puncturing unit 300 is disengaged and withdrawn from the trocar 70. As soon as practical, within a few minutes of elapsed time, detachable unit 200 is twisted and locked onto the trocar top portion 80. When Ready Light 240 lights up on detachable unit 200, indicating a proper connection between the detachable unit and the trocar as well as between tissue and electrode, the Start Button may be pushed. The In Progress Light will light up for a duration of time during the RF energy delivery to the electrodes. After a predetermined dosage of energy has been applied, the Finished Light will automatically come on indicating the treatment has been completed.

While RF energy can be applied to the edges of the surgical incision or perforation of the peritoneum at any time while the incision or perforation is still open, the above procedure is preferably accomplished within the first few seconds to a few minutes after creating the surgical intrusion. More preferably, the treatment should be accomplished within 30 seconds. After the Finished Light turns on, the detachable unit is disengaged from the trocar. The surgeon proceeds with the laparoscopy or laparotomy or other tasks using the trocar. Optionally, the surgeon repeats the RF treatment procedure subsequent to completion of the task for additional tissue treatment.

The system embodiment of FIG. 1A provides a bipolar electrode arrangement and a fully self-contained detachable unit 200 which contains the RF circuitry, control circuitry, and battery power source. There are other workable variations of this system. For example, instead of a bipolar electrode configuration, a monopolar electrode configuration may be employed. Instead of a self-contained detachable unit containing the power source, control circuitry, and RF circuitry, any one or all of these elements may be located outside the detachable unit.

Figure 3:
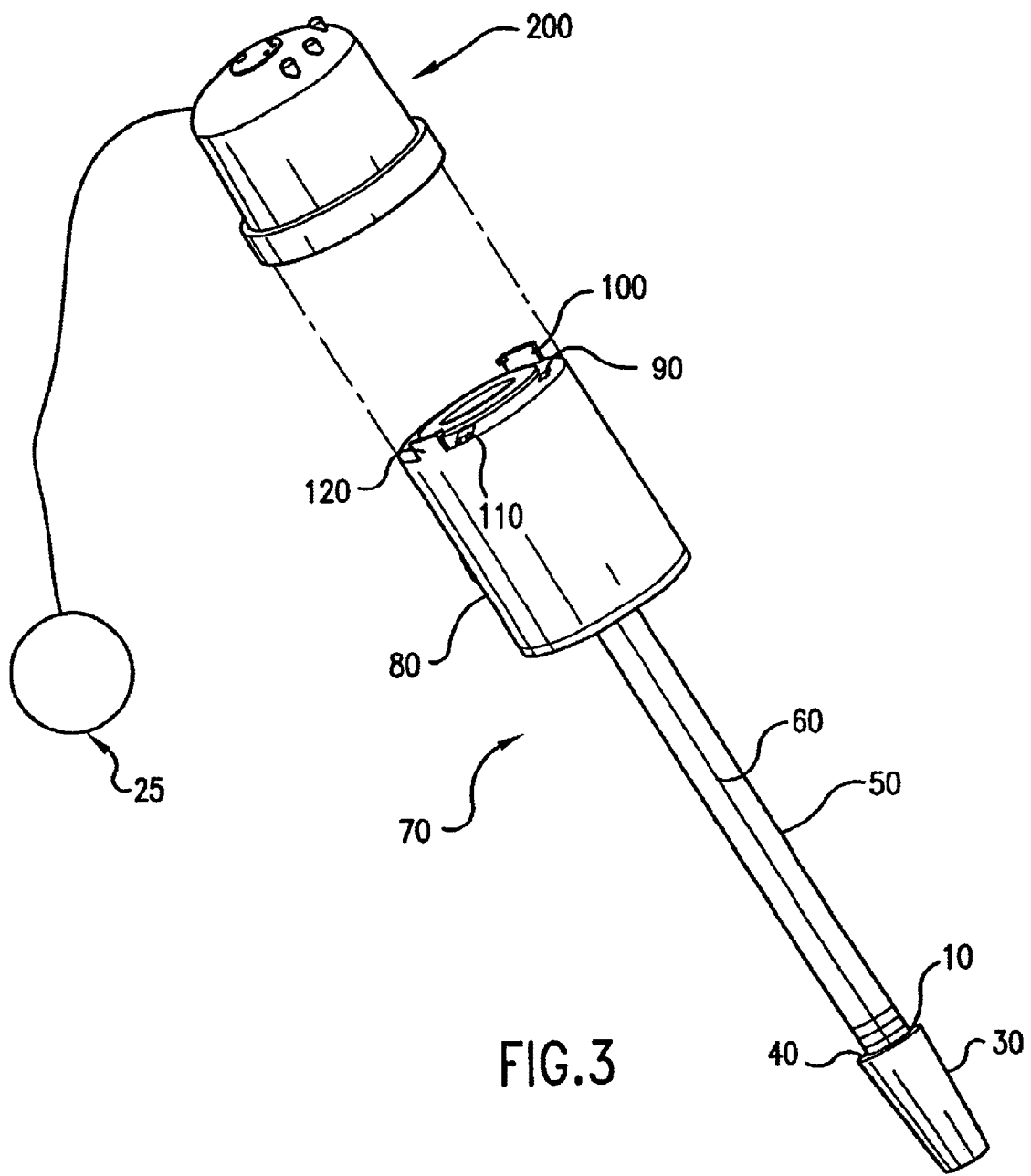
FIG. 3 shows a perspective view of the trocar based RF energy delivery system having a top detachable RF unit and a trocar sleeve which has a monopolar electrode arrangement, in accordance with the present invention.

FIG. 3 illustrates an alternative embodiment of the present invention system using a monopolar electrode configuration. Here, there is only one electrode 10 which is the active, heat-inducing electrode. Return electrode 25 has a large surface area and is placed somewhere on the body generally using a conductive gel. The impedance presented by the body-to-return-electrode interface should be orders of magnitude smaller than presented by the body-to-active-electrode interface.

Figure 4:
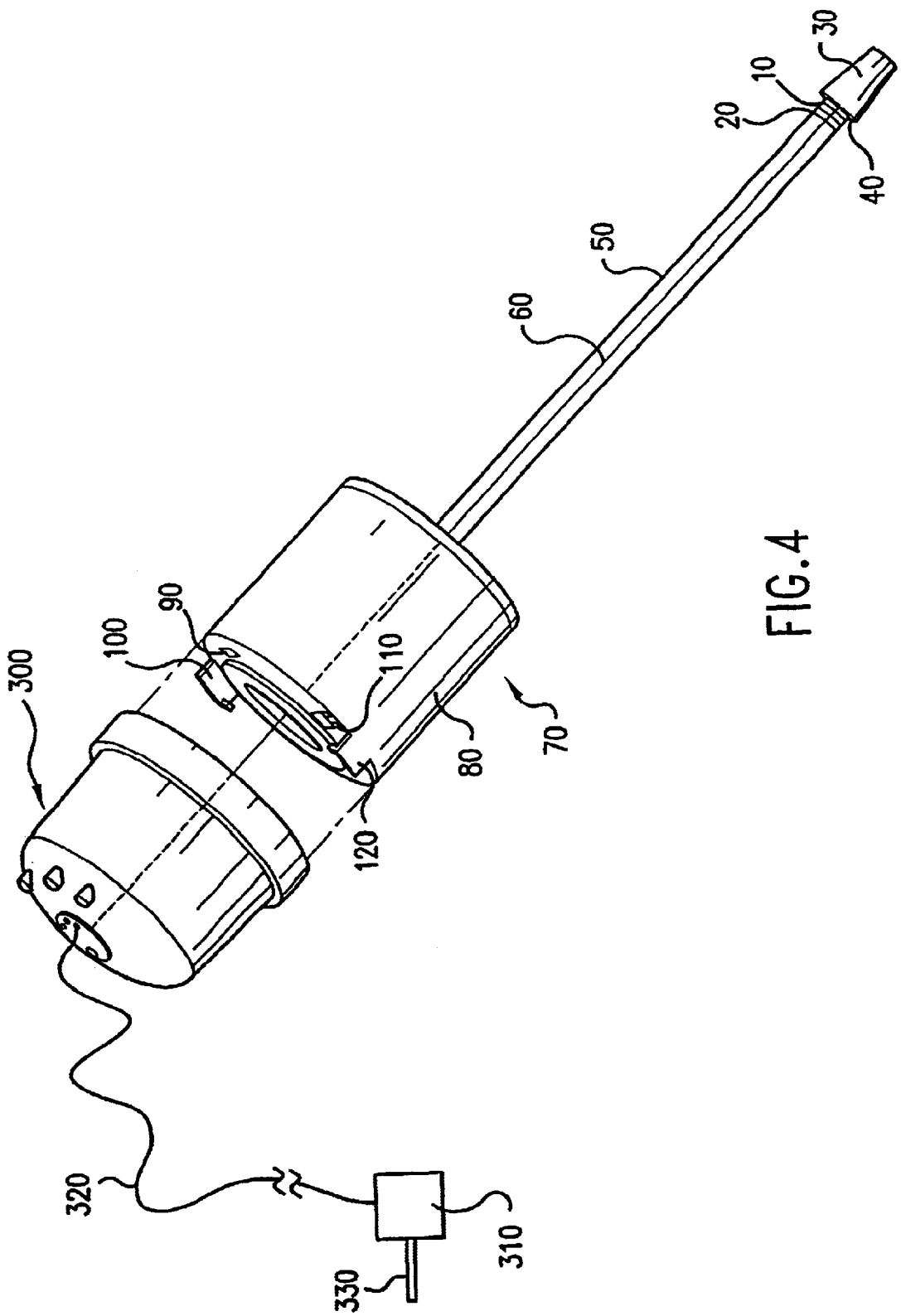
FIG. 4 shows the trocar based RF energy delivery system with an external power supply and a remotely located RF unit, in accordance with the present invention.

FIG. 4 illustrates another variation of a bipolar electrode configuration having an external box 310 containing the control circuitry, the RF circuitry and power derived from an AC-wall outlet source 330. Detachable unit 300 has status lights but minimal circuitry. Conductor cord 320 has multiple conductors and may be disconnected from the external box 310 and from detachable unit 300. This allows detachable unit 300 and conductor cord 320 to be cleaned and sterilized using known sterilization methods such as autoclaving, ethylene oxide gas sterilization, irradiation, etc.

Figure 5:
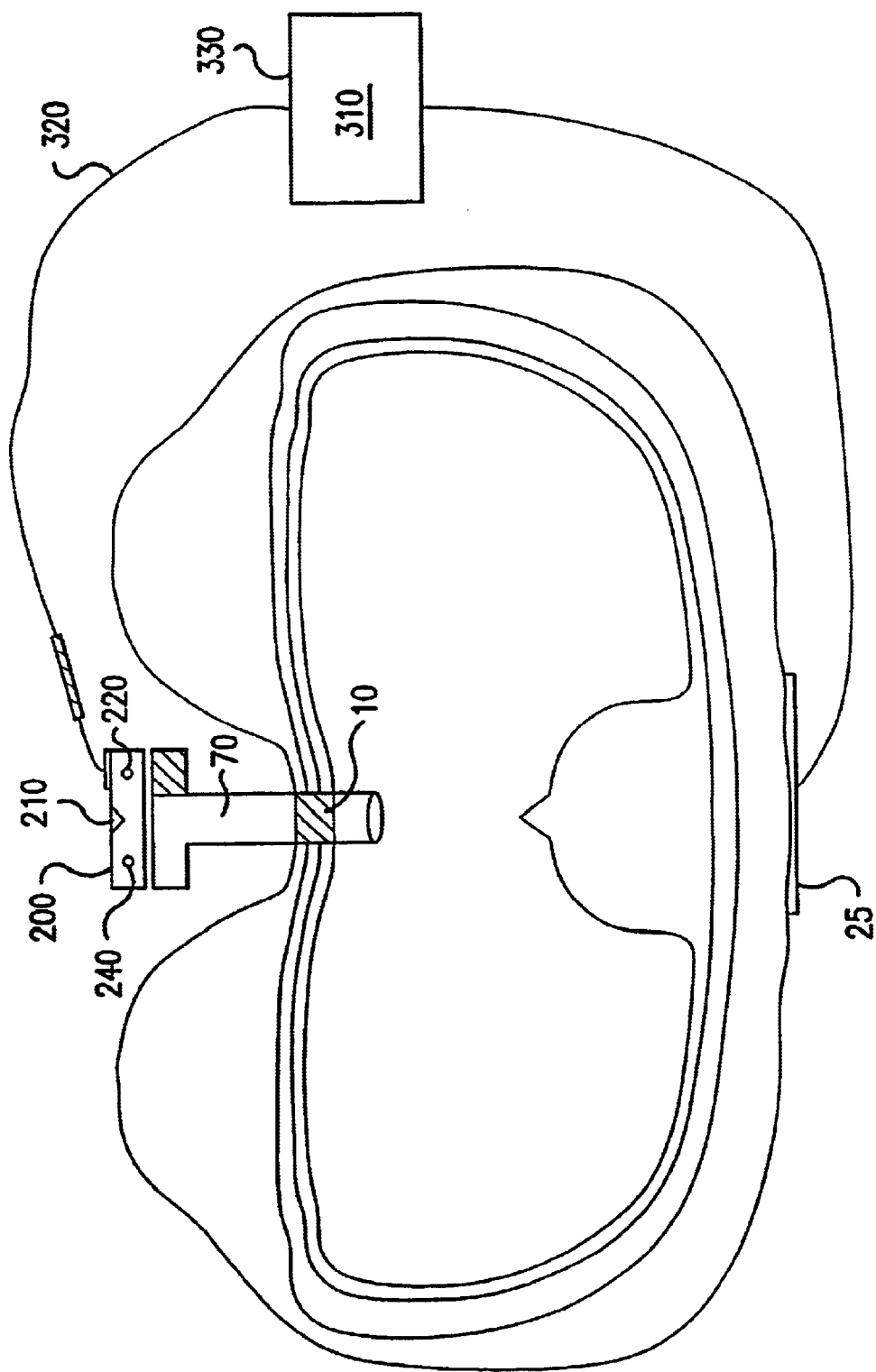
FIG. 5 shows a cross-sectional view of a monopolar trocar based RF heat delivery system with an external power supply and a remotely located RF unit, in accordance with the present invention.

FIG. 5 is a schematic cross-sectional illustration of a system inserted into the abdomen which is similar to the configuration of FIG. 4 in that all circuitry is external to the detachable unit. The difference is that the system in FIG. 5 is a monopolar, not bipolar, electrode configuration.

Figure 9:
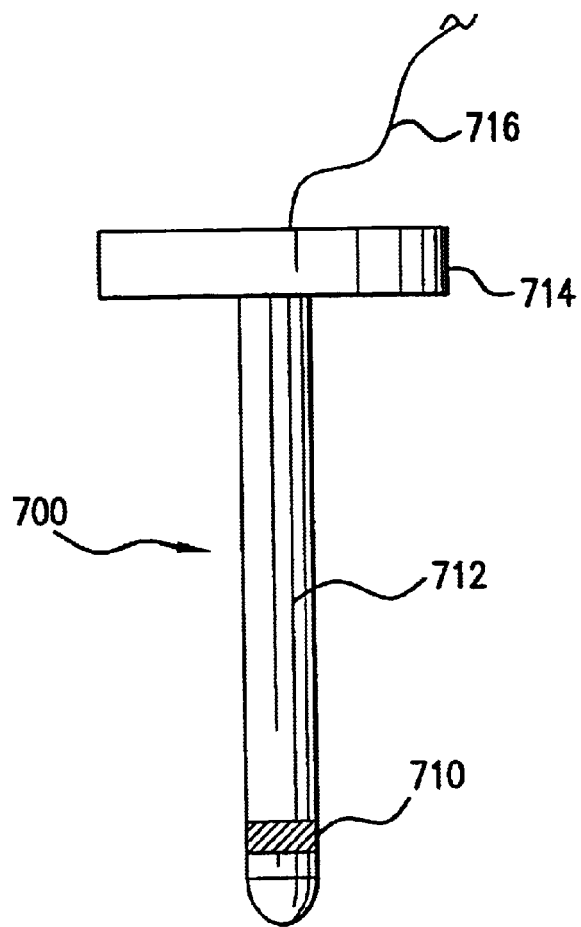
FIG. 9 is a side view of an electrode-carrying rod according to an alternative embodiment of the invention.
Figure 10:
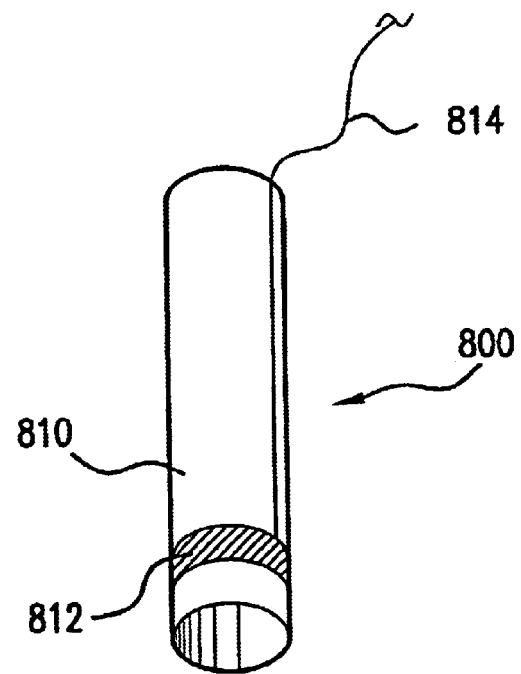
FIG. 10 is a side view of an electrode-carrying sleeve according to a further alternative embodiment of the invention.

As illustrated in FIGS. 9 and 10, electrodes may be provided alternatively on accessory devices in order to achieve the advantage of the present invention without a specially designed trocar. In particular, rod 700, as shown in FIG. 9, includes at least distal electrode 710 mounted on shaft 712. Shaft 712 is selected in diameter and length so as to cooperate with an existing trocar to position electrode 710 distally with respect to the trocar cannula in order to apply treatment as described herein. Handle 714 is provided on the proximal end of shaft 712 in order to limit the depth of insertion into the trocar and to provide a convenient means for gripping. Wire lead 716 may be provided to communicate with RF energy sources as described herein above. Sleeve 800, shown in FIG. 10, provides a further alternative for adapting a conventional trocar to the present invention. Sleeve 800 includes cylindrical member 810 with at least one electrode 812 mounted thereon. Wire lead 814 provides communication with the RF energy source. Cylindrical member 810 is sized both in internal diameter and length so as to be readily positioned over the cannula of the conventional trocar to distally position electrode 812 in order to treat the cut edge of tissues as described herein. Both rod 700 and sleeve 800 are shown herein with a single distal electrode. Persons of ordinary skill in the art will appreciate that either embodiment may be provided in a monopolar or bipolar configuration in accordance with the teachings of the present invention.

Incisions are the second type of common surgical injury to the peritoneum. These produce wounds that are larger than with laparoscopic surgery. Nonetheless, the method of inhibiting adhesion formation using application of RF induced heat can also be employed to treat the wound edges during open chest or open abdominal surgery.

Figure 6:
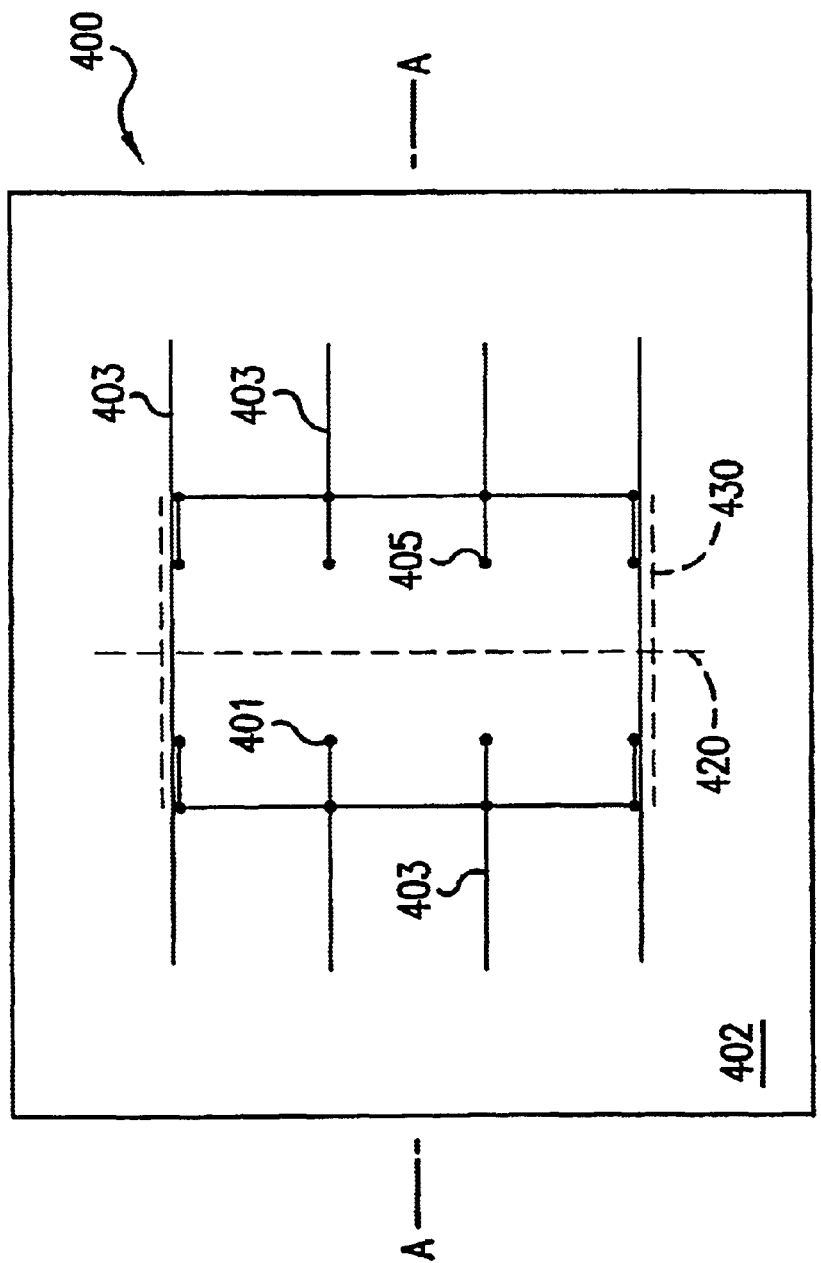
FIG. 6 shows an uncut array of electrodes on a sheet, which sheet is used in RF treatment of surgical incisions, in accordance with the present invention.

FIG. 6 illustrates the device used to treat injured incised tissue in conjunction with such open surgery in order to inhibit post-surgical adhesions. Heating sheet 400 is made from an insulating material, for example, a medical grade plastic Mylar®, Lexan®, PET, plexiglass, etc. Multiple pairs of electrodes 401 are imprinted on nonconductive sheet 402. The multiple electrodes are connected by conductors 403. Each pair of electrodes 401 when connected by conductor 403 can act as a bipolar electrode arrangement. Nonconductive sheet 402 can be cut using conventional instruments such as a scissors or scalpel. Conductors 403 connect to electrodes 401 such that these electrodes can be energized when conductors 403 are connected to an appropriate source of energy.

During open surgery, the adhesion prevention electrode array sheet is used as follows. Before an incision is made into the target, sheet 400 is placed on the skin of the patient at the site where the incision will be made. The surgeon cuts the sheet at the incision lines 420 and 430, then the skin underneath, and then the underlying tissue. Next, the cut edge 420 of the sheet 400 is folded such that the cut peritoneal surface is covered by the cut edge of the sheet.

Figure 7:
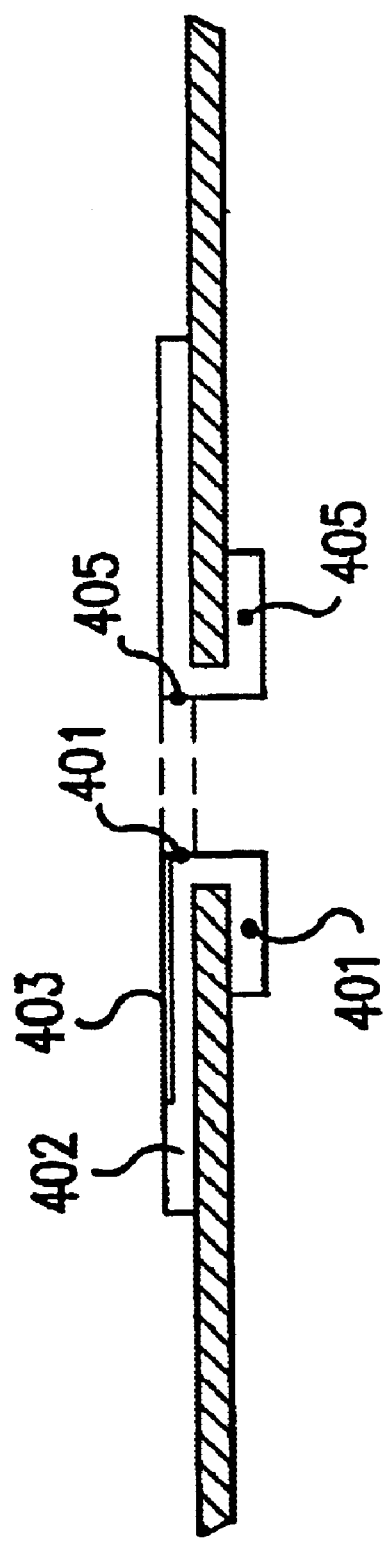
FIG. 7 shows a cross-sectional view of the electrode array sheet at A—A, after the surgeon has cut the sheet, and folded the sheet under the skin, in accordance with the present invention.

FIG. 7 shows the sheet after it has been cut and folded over the skin and peritoneum. One row of electrodes will contact the skin surface and the other row of electrodes will be tucked underneath contacting the peritoneum. Next, RF energy is activated and transmitted through a conductor 403, and to set of electrodes 401. When the treatment is completed, the next set of electrodes 405 is activated until the entire injured peritoneal surface is treated. Alternatively, rather than using sheet 400 to treat incisions in open surgery, a wand-like instrument, such as shown in FIG. 11, may be used alone to treat precise portions of tissue edges by contacting the tissue with preferably bipolar electrodes.

Referring to FIG. 11, wand-like instrument 900 includes an elongated handle with distal and proximal ends and having a main body portion 912 with a diameter adapted for comfortable hand manipulation. Distal tip 914 has a generally L-shaped configuration to facilitate guiding of tissue edges along bipolar electrodes 916. Although illustrated in a bipolar embodiment, persons of ordinary skill in the art will appreciate that based on the teachings contained herein a single electrode tip with a remote electrode may be used for a monopolar device. Also positioned on distal tip 914 are thermocouple 918 and saline port 920. Saline or a similar liquid can be fed through the port 920 to lubricate the smooth movement of the tip 914 over the tissue. Power connection 922 and thermocouple 924 are provided at the proximal end of handle 912.

Another aspect of the present invention are systems to measure and control the dosage of RF energy applied to tissue. In one embodiment, the change in tissue impedance may be used as a parameter to determine the treatment completion. Instantaneous impedance of the tissue may be determined by using the same set of RF electrodes used to apply the RF energy to injured tissue. The impedance may be determined using known methods dependent on whether the energy source is a constant voltage or constant current source. If a constant voltage source is used, the change in current pulse may be used to determine the impedance. Similarly, if a constant current source is used, the change in voltage over the duration of the test pulse may be used to calculate the impedance. When a predetermined tissue resistance is reached, for example, as a percentage of the initial tissue resistance, the RF generator is turned off.

A more sophisticated version using impedance measurements measures the total energy dissipated into the tissue over time. The instantaneous impedance values may be measured to calculate instantaneous power and total cumulative energy dissipated into the tissue. When the target cumulative energy is reached, the RF generator is turned off. Such energy calculation is well known in the art, in particular in the cardiac pacing industry, for measuring cardiac lead impedance and energy consumption.

In another embodiment the temperature of the treated tissue may be monitored using a temperature measuring device such as a thermocouple. When the tissue is heated to a certain temperature, for example, between 65 to 100° C., the RF generator is turned off.

In yet another embodiment treatment time elapsed may be used as a general parameter. When the treatment duration reaches a predetermined level, the RF generator is turned off.

In yet another embodiment, in accordance with the present invention, a combination of both time and temperature are used to regulate the amount of RF energy used to reduce the incidence of post-surgical connective tissue adhesions. Achieving a set temperature and maintaining the target tissue at that set temperature for a predetermined period results in minimal adhesions. Temperatures between about 65 to 100° C. and treatment times ranging from 5 to 25 seconds provide beneficial results.

The system could be battery operated and be constructed of disposable materials. Alternatively, the system may be contained in an external box with an RF generator, thermometer circuitry, clock and feedback loop to control temperature and to end the treatment. In a preferred embodiment the thermocouple is attached to a delivery system structure near the active electrode providing RF energy. The energy supplied is determined by a pre-set temperature level and this level may be maintained for a predetermined duration through a temperature feedback loop.

As will be appreciated by persons of ordinary skill in the art, alternative means for heating tissue to the appropriate levels for the appropriate times as described herein may be employed. For example, direct resistive heating may be utilized by substituting resistive heating elements for the electrodes in the various embodiments described herein. The description of RF energy in connection with preferred embodiments disclosed herein is not intended as limiting of the heating means which may be employed.

As depicted in FIG. 2 the control indicator system comprises a Start Button and three lights. The Ready Light is illuminated when the system has completed a successful check to ensure appropriate tissue contact. When the user presses the Start Button, the In Progress Light glows indicating that RF energy is being supplied to the electrodes. During this time, the RF generator heats the tissue to a pre-set temperature, which is measured by the thermocouple, and maintains that temperature until an internal timer turns the generator off. Once the generator is turned off, the Finished Light illuminates indicating that the treatment is over. Other signals such as audio signals could be used instead of or in addition to lights to indicate progress of the treatment.

Figure 8:
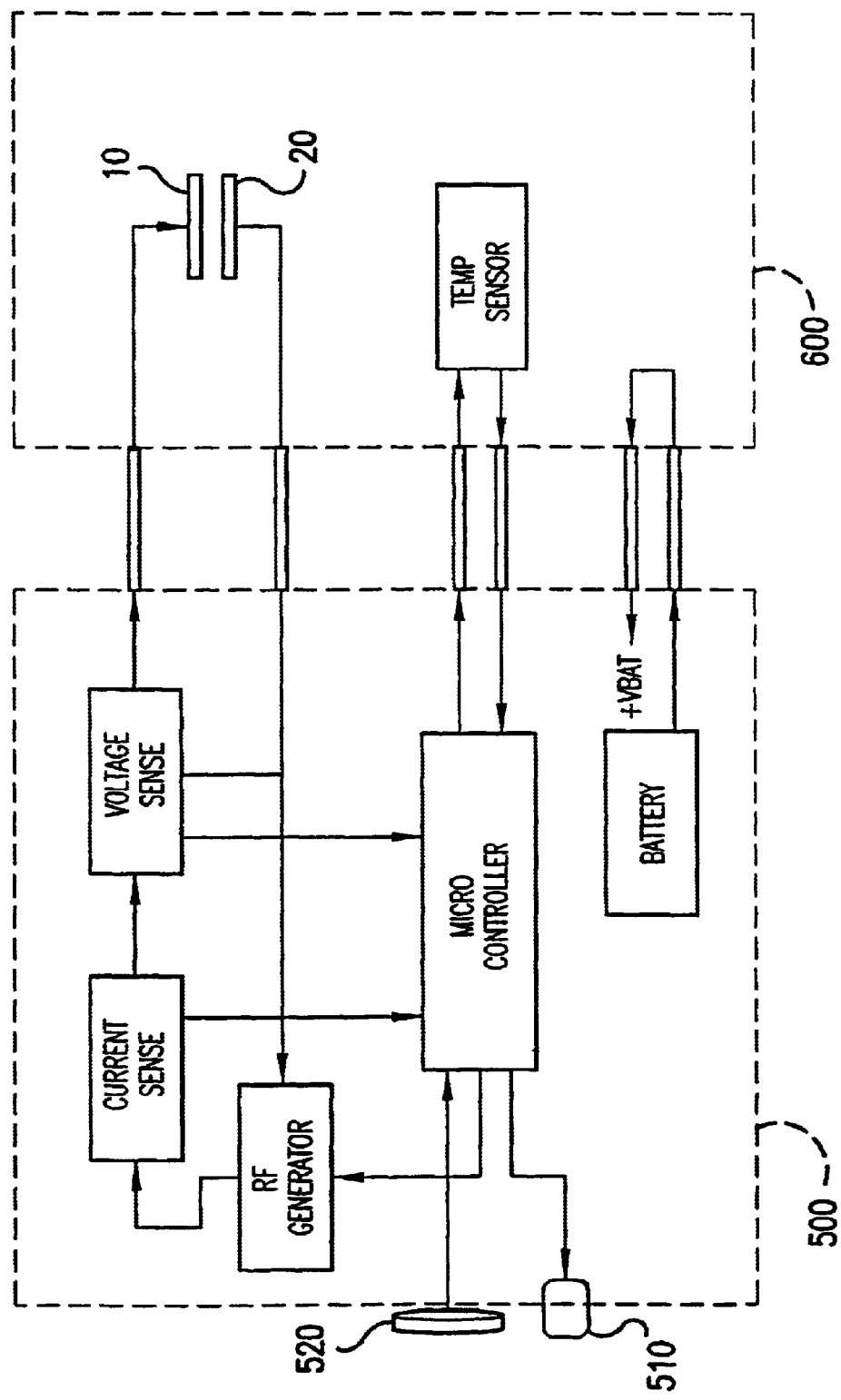
FIG. 8 is a generalized block diagram of one embodiment of an RF delivery system showing the feedback system with a temperature sensor.

FIG. 8 is a generalized block diagram of one embodiment of an RF delivery system. Section 500 contains circuitry for an RF generator, a current and voltage sense means, a microcontroller and a battery. Section 500 contains starting means 520, which may be a start button 210 as shown in FIG. 2. Section 500 also has indicator means 510 which may be an array of lights, 220, 230, 240 as shown in FIG. 2. Alternatively, the indicator means may be various distinct audio signals. Section 600 represents the delivery structure such as the trocar sleeve 70 or a non-conductive sheet 400 which contains the electrodes. Section 600 contains two electrodes 10 and 20 providing a bipolar electrode configuration. Section 600 also contains a temperature sensor, for example, a thermocouple.

The voltage and current sensing means provides instantaneous voltage and current as well as tissue temperature values to the microcontroller. If the tissue temperature does not exceed a predetermined value, the microcontroller increases the energy level delivered by the RF generator. If the tissue temperature exceeds a predetermined value, the microcontroller decreases the energy level delivered by the RF generator. The RF energy delivered to the tissue is thus continuously altered within this feedback loop to maintain a predetermined tissue temperature.

The following examples summarize results of animal studies which indicate that the control parameters such as change in tissue impedance, change in tissue temperature, and time of treatment may be used to determine when the treatment cycle should be ended.

EXAMPLE 1

Using Impedance Change as the Indicator of Treatment Completion

A study was conducted using rabbits to determine the effects of applying RF energy to the impedance of the peritoneal tissue and whether impedance may be used to indicate treatment completion. For the RF energy treated group (n=3), an incision was made about the midline on the dorsal surface of the rabbit. A single trocar was introduced into the abdomen of each animal. Using a monopolar assembly, RF energy was applied to the peritoneum until the measured tissue impedance was above three times the initial impedance. To mimic a surgical procedure that would be performed laparoscopically, a cotton swab was used to roughen the serosa of the small bowel. The incisions were sutured with a bioabsorbable suture material. One week later, the treated and control animals were sacrificed and a necropsy performed. The same procedure was performed on four control animals except that no RF energy was applied to their peritoneums.

None of the three animals that were treated with RF energy formed adhesions. But three of the four control animals did form adhesions. One had mild adhesions to the abdominal wall, while two had extensive, highly vascularized adhesions to the bladder, bowel and abdominal wall. Impedance may, therefore, be used as a treatment completion indicator.

EXAMPLE 2

Using Temperature as the Indicator of Treatment Completion

A rabbit study was conducted to determine the effects of monitoring tissue temperature to control the amount of RF energy applied to the peritoneal tissue and the effect on the incidence of post-operative adhesions. A small midline incision was made on the dorsal surface of each of the three treated rabbits. Immediately after a trocar was inserted into the incision, RF energy was applied to the injured tissue until the tissue temperature reached a set trigger point of 100° C.; a monopolar assembly was used. After each animal's serosa of the small bowel was roughened using cotton swabs, the incision was sutured. One week later, the animals were sacrificed and the incidence of adhesions to the port site and organs was determined. Two of the three animals showed no signs of adhesions while the third had grade 2 adhesions (rated 0 to 5 with 5 being the worst).

EXAMPLE 3

Using Time as the Indicator of Treatment Completion

Rabbits were used to determine the effects of using time to control the amount of RF energy applied to the peritoneal tissue and the effect on the incidence of post-operative surgical adhesions. Two small incisions were made on either side of the dorsal midline surface of the rabbit's body (n=2). One trocar was inserted into each incision, and RF energy was applied for 60 seconds. The rest of the procedure is as described in Example 2. One week later, the animals were sacrificed and the extent of adhesion formation at the port site and to the organs was assessed. One animal exhibited no adhesions to either of the port sites or to any of the abdominal organs. The other animal had no adhesions to one port site but at the other port site, there was herniation of the small bowel, accompanied by a grade 2 adhesion.

EXAMPLE 4

Using a Combination of Temperature and Time as the Indicator of Treatment Completion: Rabbit Study A rabbit study was conducted to determine the effects of applying RF energy on the incidence of connective tissue adhesion formation following perforation of the peritoneum. After the rabbits were anesthetized, two trocars were inserted into the abdomen of each rabbit. RF energy was applied through each trocar hole immediately after insertion maintaining the temperature at 75° C. for a duration of either 5, 10, or 15 seconds. The serosa of each animal was roughened using cotton swabs before the holes were closed. One week after the RF treatment, the rabbits were sacrificed and examined for adhesions to the abdominal cavity. The rabbits had no adhesions to either the trocar site or to any peripheral sites. Evaluating the blanching of tissue caused by the RF treatment, it was concluded that applying RF energy for 10 seconds was an appropriate treatment duration.

EXAMPLE 5

Using a Combination of Temperature and Time as the Indicator of Treatment Completion: Pig Study The above study was also conducted in pigs in order to determine the effects of RF energy to the peritoneum on the incidence of adhesion formation. In these studies the standard treatment duration was 75° C. for 10 seconds. Four trocars, three 5 mm and one 12 mm in length, were inserted into a pig's abdominal wall. Upon insertion of each trocar, RF energy was immediately applied to the edges of the perforated peritoneum. The animal's serosa was roughened using sterile cotton gauze before the entry sites were closed. Viewing through a second-look laparoscopy one week later, no adhesions were found in either the trocar sites, the peripheral abdominal wall sites, or the animal's small bowel.

A control study was conducted by performing the same procedure on another pig for which the two trocar holes were not treated with RF. One week later, observed during a second-look laparoscopy, there were highly vascularized adhesions to one of the trocar entry sites connecting the abdominal wall to the internal organs.

It will now be readily apparent to those skilled in the art that various modifications may be made to the systems and methods disclosed herein utilizing RF heating to reduce post-surgical adhesions without departing from the spirit and scope of the invention. The scope of the invention shall not be limited to the embodiments described in the specification but shall instead be defined by all variations and equivalents as embraced by the appended claims.

What is claimed is:

1. A system for treating cut edges of tissue in surgical perforations comprising:
   at least one member configured and dimensioned to have a surface, which surface may be placed on the cut edge of the tissue;
   at least a first energy delivery element disposed on said member surface, positioned to be in contact with the cut edge when said member is positioned adjacent to the cut edge of tissue; and
   an RF energy source communicating with the energy delivery element which applies energy to the cut edge in a controlled manner to reduce post-surgical complications,
   wherein the member is either a trocar having a hollow channel further comprising a detachable unit, which mounts on a proximal end of said member and produces the controlled RF energy and wherein the energy delivery element is at least one electrode,
   wherein the detachable unit has an electrical contact and the trocar has an electrical contact,
   whereby the controlled RF energy is transmitted from the detachable unit to the delivery electrode located when the two electrical contacts are in electrical communication,
   wherein the detachable unit further comprises an attachment means used to lock and unlock the detachable unit to said trocar,
   wherein said attachment means are protruding latches that lock and unlock the detachable unit to the sleeve by twisting the detachable unit, relative to the position of the trocar, in one direction and in the opposite direction, respectively, or
   the member is a non-conductive sheet.

2. A system according to claim 1, wherein the trocar has a second electrode providing a bipolar electrode configuration, wherein the second electrode is a ring electrode and the first electrode is a ring electrode.

3. The system according to claim 2 wherein the spacing between the two ring electrodes is between 0.5 and 3.0 millimeters.

4. The system according to claim 3 wherein the first ring electrode has a width between about 0.5 and 3.0 millimeters; the second ring electrode has a width of between about 0.5 and 3.0 millimeters; and the width of the first electrode is substantially smaller than the width of the second electrode.

5. The system according to claim 1 wherein the trocar sleeve comprises:
   a hollow conical section on the distal end of the trocar sleeve, the conical section having one end that has a larger diameter portion and a distal end having a smaller diameter portion;
   a hollow, rod-like sleeve portion;
   a hollow cylindrical portion having a substantially larger diameter than the rod-like sleeve portion;
   wherein the conical section connecting its larger diameter portion to one end of the rod-like portion; the cylindrical portion connects to the other end of the rod-like portion such that a channel is created through the entire length of trocar; a protruding lip formed between the rod-like portion and the conical portion; and wherein the first electrode is positioned close to the lip.

6. The system according to claim 5 further comprising:
   a return electrode that is not attached to the trocar.

7. The system according to claim 5 wherein the trocar sleeve does not have any return electrodes.

8. The system according to claim 1 wherein the sheet has multiple electrodes positioned on the sheet such that when the sheet is cut, the electrodes are in close proximity to the tissue incision.

9. The system according to claim 1 wherein the sheet is an insulating material having one side weakly adhesive to tissue or skin.

10. The system according to claim 1 wherein the detachable unit comprises:
    means for starting RF treatment;
    means for indicating sufficient electrode contact with tissue;
    means for indicating that RF treatment is ongoing; and
    means for indicating that RF treatment has been completed.

11. The system according to claim 10 wherein the means for starting RF treatment is a push button, and the means for indicating sufficient electrode contact with tissue, the means for indicating that RF treatment is ongoing, and the means for indicating that RF treatment has been completed are each an indicator light.

12. The system according to claim 10 wherein the means for starting RF treatment is a push button, and the means for indicating sufficient electrode contact with tissue, the means for indicating that RF treatment is ongoing, and the means for indicating that RF treatment has been completed are each an indicator audio signal.

13. The system according to claim 1, wherein said at least one member comprises a sleeve having distal and proximal ends, wherein said electrode is positioned on said sleeve adjacent the distal end and wherein the sleeve is configured and dimensioned to have an internal diameter and length to be received over a cannula of a trocar and place said electrode adjacent the cannula distal end.

14. The system according to claim 1, wherein said at least one member comprises an elongate wand-like member having distal and proximal ends, with a handle portion configured and dimensioned for gripping by hand; and said energy delivery element is disposed at the distal end wherein said distal end includes a distal tip shaped to guide the tissue edge along said energy delivery element and wherein a thermosensor and a fluid delivery port are disposed on said tip.

15. The system according to claim 14, wherein said energy delivery element comprises at least one RF energy delivery electrode.

16. A method for treating injured tissue in conjunction with use of a trocar comprising:

placing an obturator within the trocar sleeve to form an assembly;

using the assembly to puncture the abdominal wall;

withdrawing the obturator from the trocar sleeve;

placing a detachable unit over the exposed portion of the trocar sleeve such that there is electrical contact between the detachable unit and the sleeve;

providing controlled RF energy from the detachable unit to an electrode located on the trocar sleeve to heat the proximately located injured tissue;

detaching the detachable unit; and performing a surgical function through the trocar sleeve.

17. A method for treating incised tissue comprising:

placing a surgical sheet over the site of incision having a plurality of electrodes embedded in the sheet, which electrodes are still electrically accessible on either side of the sheet;

cutting through the surgical sheet and underlying tissue;

folding the surgical sheet in a manner to position the plurality of electrodes close to the incision; and applying controlled RF energy through the electrode to heat the proximately located, incised tissue.

* * * * *